(12) United States Patent
Fujiwara et al.

(10) Patent No.: US 7,708,462 B2
(45) Date of Patent: May 4, 2010

(54) TRANSMISSION IMAGE CAPTURING SYSTEM AND TRANSMISSION IMAGE CAPTURING METHOD

(75) Inventors: Koichi Fujiwara, Takarazuka (JP);
Osamu Toyama, Kakogawa (JP);
Sumiya Nagatsuka, Hino (JP)

(73) Assignee: Konica Minolta Holdings, Inc., Tokyo (JP)

( * ) Notice: Subject to any disclaimer, the term of this patent is extended or adjusted under 35 U.S.C. 154(b) by 110 days.

(21) Appl. No.: 12/215,793

(22) Filed: Jun. 30, 2008

(65) Prior Publication Data

US 2009/0008581 A1    Jan. 8, 2009

(30) Foreign Application Priority Data

Jul. 6, 2007    (JP)    ............................... 2007-178396

(51) Int. Cl.
*H05G 1/60* (2006.01)
*A61B 6/08* (2006.01)
*G01D 18/00* (2006.01)

(52) U.S. Cl. ........................... 378/207; 378/21; 378/22; 378/23; 378/24; 378/25; 378/26; 378/206

(58) Field of Classification Search .................... 378/21, 378/22, 23, 24, 25, 26, 27, 196, 197, 206, 378/207

See application file for complete search history.

(56) References Cited

U.S. PATENT DOCUMENTS

| | | | | |
|---|---|---|---|---|
| 6,227,704 | B1 * | 5/2001 | Bani-Hashemi et al. | 378/206 |
| 6,402,373 | B1 * | 6/2002 | Polkus et al. | 378/207 |
| 6,402,374 | B1 * | 6/2002 | Boomgaarden | 378/207 |
| 6,435,716 | B1 * | 8/2002 | Polkus et al. | 378/205 |
| 6,447,164 | B1 * | 9/2002 | Polkus | 378/206 |
| 6,478,462 | B2 * | 11/2002 | Polkus et al. | 378/207 |
| 6,893,157 | B2 * | 5/2005 | Arakawa | 378/205 |
| 7,413,344 | B2 * | 8/2008 | Qian | 378/206 |

FOREIGN PATENT DOCUMENTS

JP       2003-061944        3/2003

* cited by examiner

*Primary Examiner*—Allen C. Ho
(74) *Attorney, Agent, or Firm*—Brinks Hofer Gilson & Lione

(57) ABSTRACT

The present invention proposes a technique capable of accurately grasping position and angle of a radiation generator at the time of image capturing. At the time of obtaining a plurality of transmission images by detecting radiation emitted from a emitting generator and passing through a specimen via a predetermined member (for example, a diaphragm) by a detector for a plurality of times while changing a relative position relation and a relative angle relation of the emitting generator to the detector, an outer-edge shape of a radiation area irradiated with the radiation on a detection surface of the detector from the emitting generator is recognized. On the basis of the outer-edge shape of the radiation area and an inner-edge shape of a predetermined member, the relative position relation and the relative angle relation of the emitting generator to the detector are obtained.

8 Claims, 14 Drawing Sheets

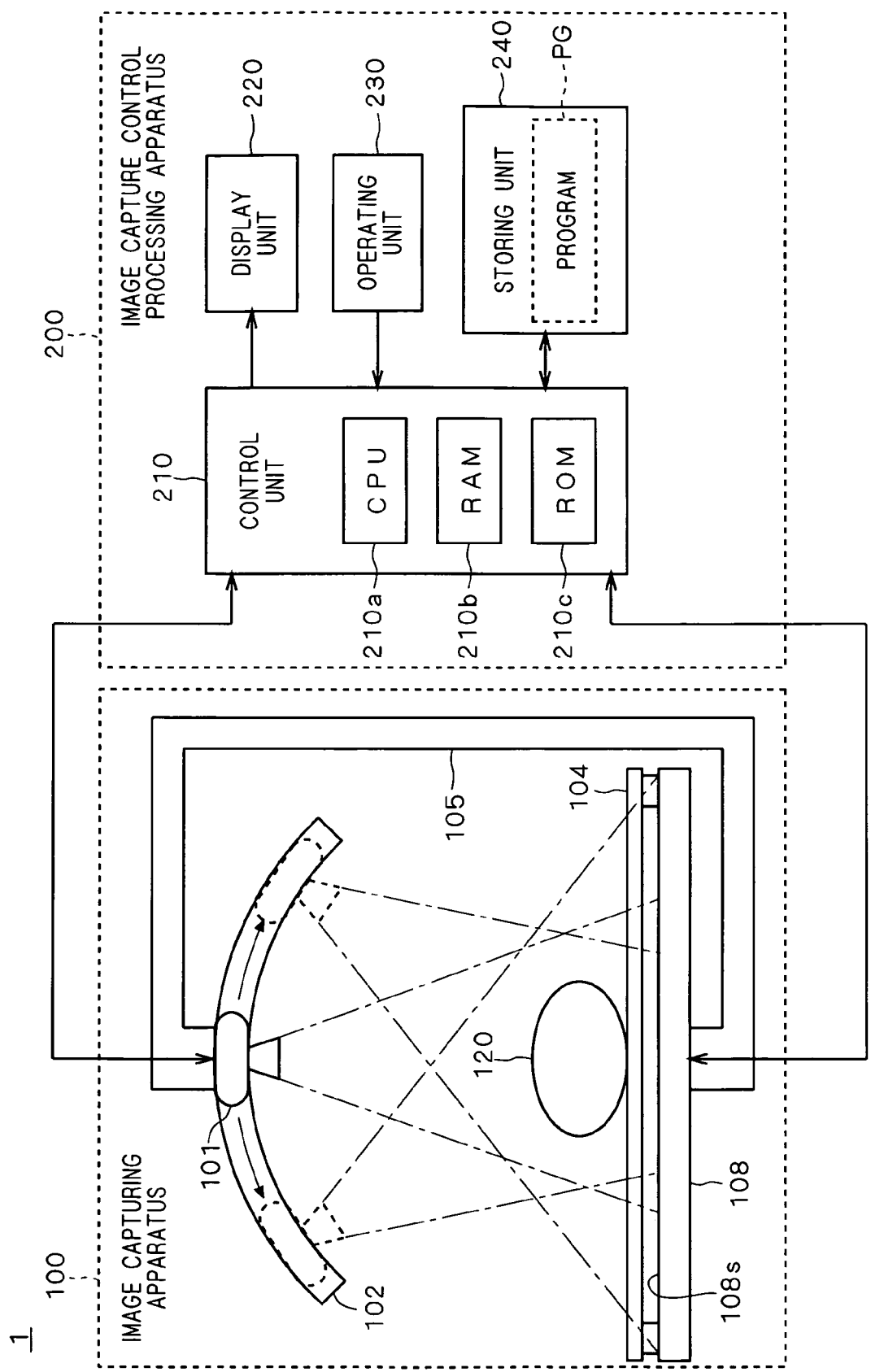

FIG. 11
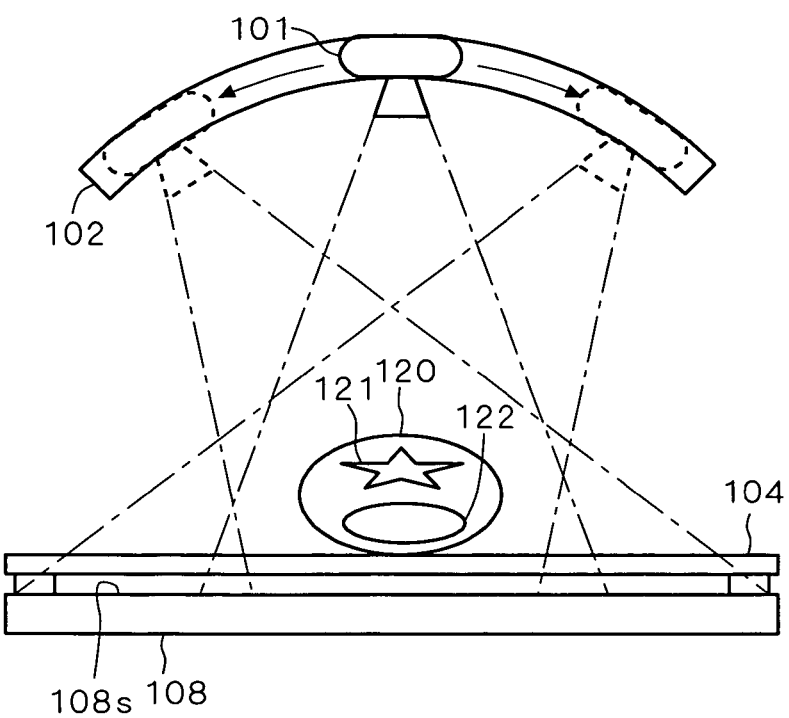
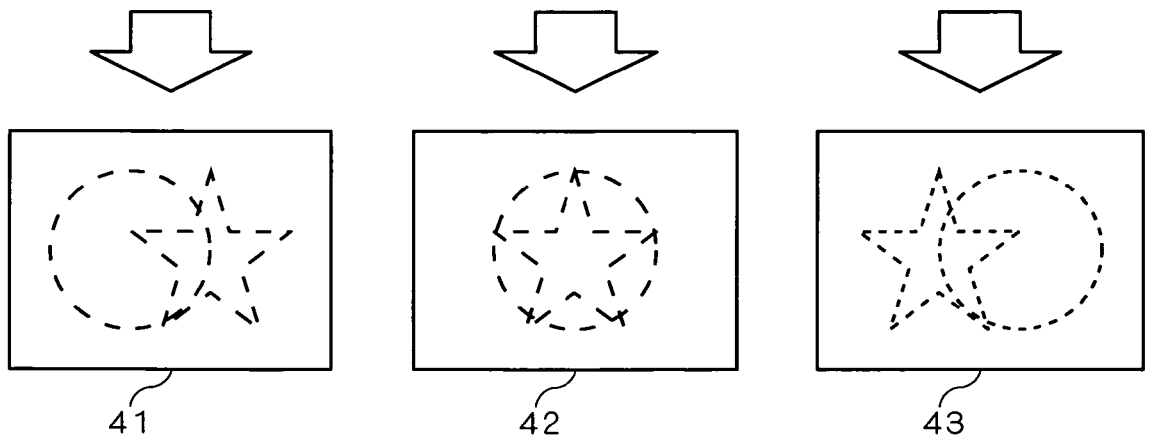

FIG. 12A
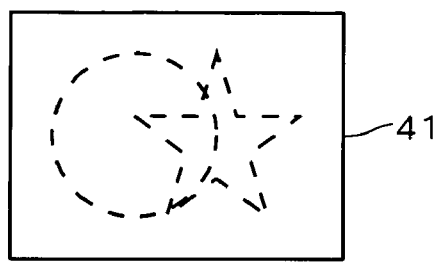
41
+
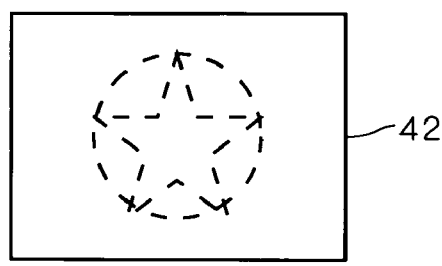
42
+
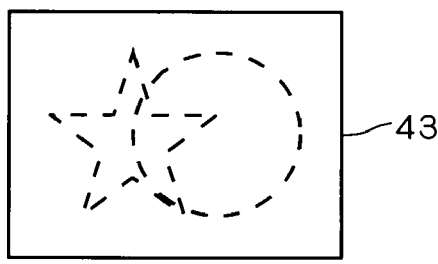
43
=
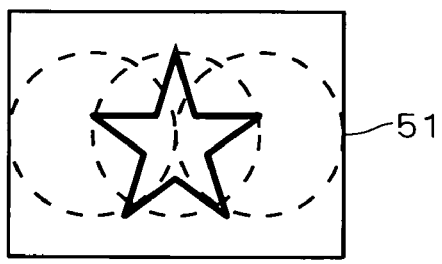
51
FIG. 12B
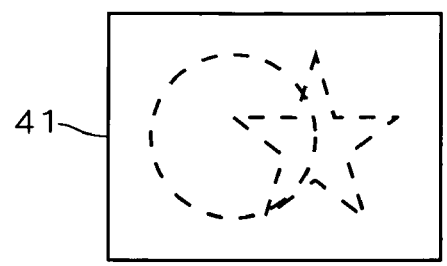
41
+
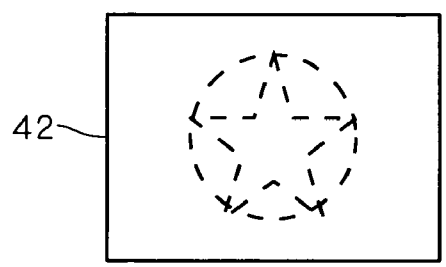
42
+
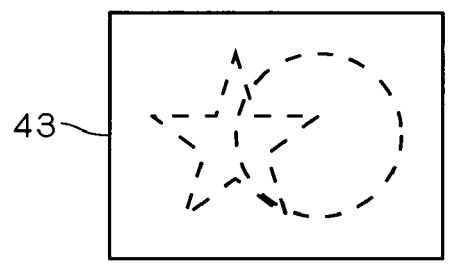
43
=
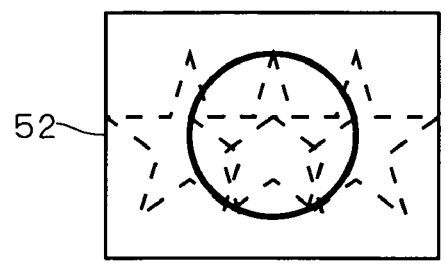
52

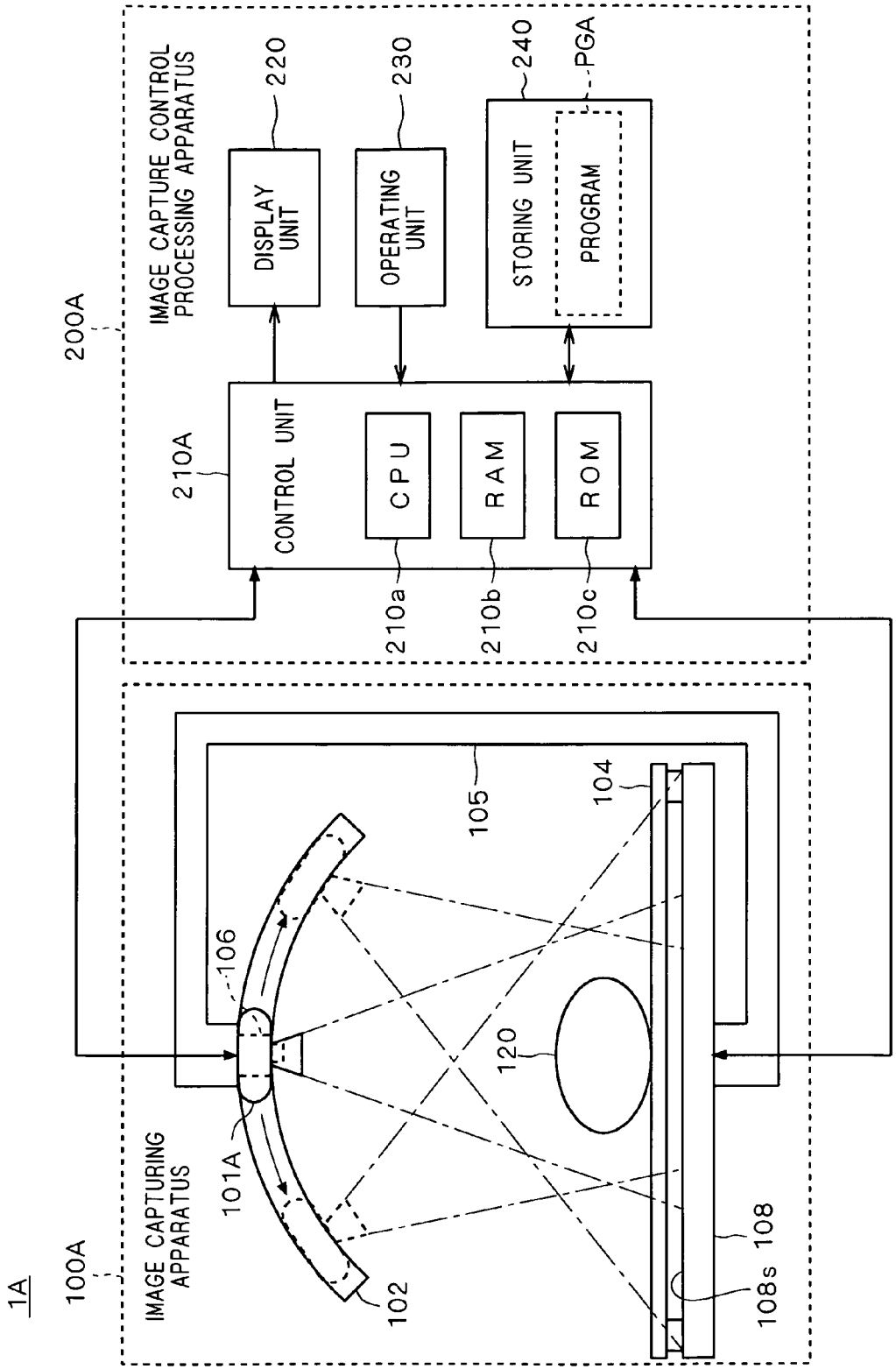

TRANSMISSION IMAGE CAPTURING SYSTEM AND TRANSMISSION IMAGE CAPTURING METHOD

This application is based on application No. 2007-178396 filed in Japan, the contents of which are hereby incorporated by reference.

BACKGROUND OF THE INVENTION

1. Field of the Invention

The present invention relates to a transmission image capturing technique.

2. Description of the Background Art

In medical fields, transmission images of a human body are captured by using X ray or the like. By reading the transmission images, diagnosis is conducted.

An X-ray diagnosing apparatus for so-called tomosynthesis is proposed, capable of observing a slice plane of a specimen at an arbitrary depth by synthesizing (reconstructing) a plurality of pieces of image data obtained by irradiating the specimen with X ray in different directions by image capturing using X ray.

At the time of capturing a plurality of projection images to generate an image of a slice plane, the position and angle of a scan system such as a part that emits radiation (for example, an X-ray tube) tend to be deviated from settings. Due to the deviation, so-called artifact such as distortion occurs in an image of a slice plane reconstructed. It is consequently very important to accurately grasp the position and angle of a part for generating radiation (radiation generating part) at the time of capturing a projection image.

To address such a problem, a technique of disposing a chart for calibration made of two microspheres, performing image capturing, and calibrating a scan system on the basis of the position of the chart for calibration in a projection image, thereby grasping the position and angle of a radiation generator more accurately and performing more accurate reconstruction has been proposed (for example, Japanese Unexamined Patent Application Publication No. 2003-61944).

However, in the technique proposed in Japanese Unexamined Patent Application Publication No. 2003-61944, calibration is performed in advance using the chart for calibration before image capturing. In the case where a different deviation occurs in the scan system at the time of image capturing, the position and angle of a radiation generator at the time of image capturing cannot be accurately grasped, and it is difficult to perform accurate reconstruction.

SUMMARY OF THE INVENTION

The present invention is directed to a transmission image capturing system.

According to the invention, the transmission image capturing system includes: a generator for generating radiation; a predetermined member for specifying a radiation path of the radiation by its inner-edge shape; a detector for detecting radiation emitted from the generator and passing through a specimen via the predetermined member; an obtaining unit for obtaining a plurality of transmission images of the specimen by detecting the radiation for a plurality of times by the detector while changing a relative position relation and a relative angle relation of the generator to the detector; and a computing unit for obtaining the relative position and angle relations on the basis of an outer-edge shape of a radiation area which is irradiated with the radiation emitted from the generator to a detection surface of the detector and the inner-edge shape of the predetermined member.

With the configuration, the position and the angle of the radiation generator at the time of image capturing can be grasped accurately.

The present invention is also directed to a transmission image capturing method of obtaining a plurality of transmission images by detecting radiation emitted from a generator and passing through a specimen via a predetermined member for a plurality of times by a detector while changing a relative position relation and a relative angle relation of the generator to the detector.

Therefore, an object of the present invention is to provide a technique capable of accurately grasping position and angle of a radiation generator at the time of image capturing.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a diagram showing a schematic configuration of an image capturing system of a first preferred embodiment;

FIG. 11 is a schematic diagram showing the principle of tomosynthesis;

FIGS. 12A and 12B are schematic diagrams showing the principle of tomosynthesis;

FIG. 13 is a diagram showing a schematic configuration of an image capturing system of a second preferred embodiment;

DESCRIPTION OF THE PREFERRED EMBODIMENTS

Figure 2A:
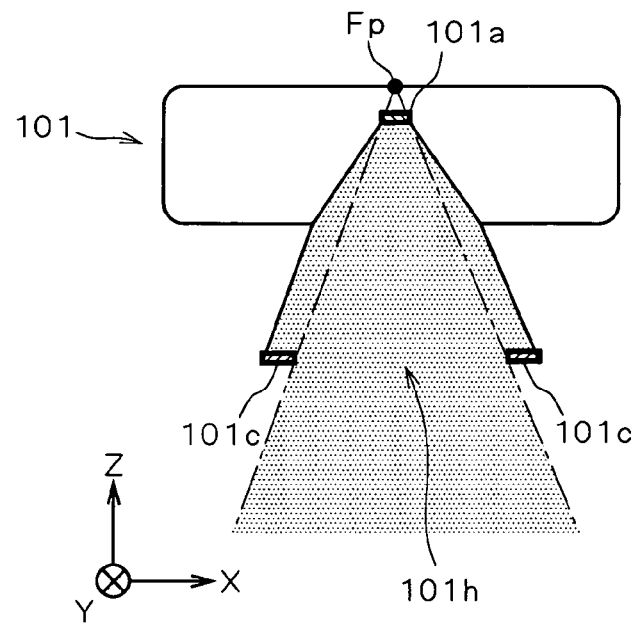
FIGS. 2A and 2B are diagrams for explaining the configuration of a emitting generator in the first preferred embodiment.

Embodiments of the present invention will be described below with reference to the drawings.

First Preferred Embodiment

Schematic Configuration of Image Capturing System

FIG. 1 is a diagram showing a schematic configuration of an image capturing system 1 of a first preferred embodiment of the present invention. The image capturing system 1 detects a distribution of radiation passing through a specimen 120 by using radiation (typically, X ray), and obtains a distribution of pixel values (transmission image), so that various information processes using the transmission image can be performed. That is, the image capturing system 1 functions as a system for capturing a transmission image (transmission image capturing system).

The image capturing system 1 includes an image capturing apparatus 100 and an image capture control processing apparatus 200. It is assumed that the specimen 120 as an object to image capturing is the body of a person to take a test. An oval in the diagram schematically expresses the body of the specimen.

The image capturing apparatus 100 has, mainly, a emitting generator 101, a guide 102, a mounting part 104, a coupling part 105, and a detector 108.

The emitting generator 101 generates and emits radiation as a kind of electromagnetic waves. It is assumed here that the emitting generator 101 generates and emits X rays. In FIG. 1 and subsequent diagrams, alternate long and short dash lines are drawn at the outer edges of the path of emission of radiation.

Figure 2B:
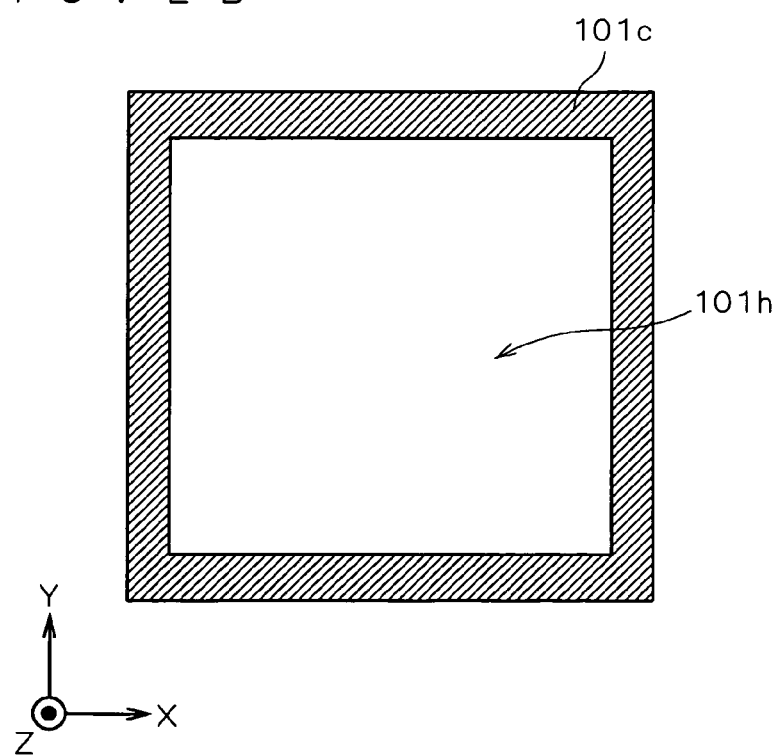

FIGS. 2A and 2B are diagrams illustrating the configuration of the emitting generator 101. In FIGS. 2A and 2B and subsequent diagrams, to clarify the azimuth relation, three axes of X, Y, and Z which cross orthogonal to each other are properly shown.

FIG. 2A is a cross section diagram schematically showing the configuration of the emitting generator 101. The emitting generator 101 is constructed by, for example, an X-ray tube and has a generating unit 101a and a diaphragm 101c. In FIG. 2A, a radiation passage area is shaded.

The generating unit 101a is a part for generating radiation, and the diaphragm 101c is provided for the generating unit 101a and functions as a predetermined member that specifies the path of radiation (radiation path) emitted from the generating unit 101a toward the specimen 120, that is, the shape of the radiation path. By disposing the generating unit 101a and the diaphragm 101c, the emitting generator 101 forms a focal point Fp of radiation (for example, focal point of an X-ray tube).

As shown in FIG. 2B, the diaphragm 101c (a hatched portion in the diagram) has, for example, an opening 101h of a square shape whose length of one side has a predetermined value, that is, an inner-edge shape. The distance from the focal point Fp to the opening 101h, specifically, the distance from the focal point Fp to the center point of the opening 101h is set to be a predetermined distance.

By the shape of the opening 101h, the outer edges of the radiation path of the radiation form a square shape. Further, the size of the square as the outer-edge shape of the radiation path increases in proportion to distance from the generating unit 101a.

Referring again to FIG. 1, the explanation will be continued.

The guide 102 extends almost an arc shape and can change the position and posture of the emitting generator 101. Concretely, the emitting generator 101 is movably coupled to the guide 102 in the extending direction and moves along the extending direction on the guide 102 according to an image capture control processing apparatus 200.

The mounting unit 104 is a part on which the specimen 120 is left at rest. The mounting unit 104 is disposed so as to satisfy a predetermined relative disposing condition with respect to the emitting generator 101 coupled to the guide 102 via the coupling unit 105. The specimen 120 is mounted within a radiation range of an X-ray emitted from the emitting generator 101. More specifically, the mounting unit 104 is fixed in a predetermined position on the side where the focal point of the arc-shaped part specified by the guide 102 is located.

The mounting unit 104 is made of a material substantially transmitting an X-ray by having small absorption of an X-ray, and X-ray attenuation coefficient (absorption coefficient) is known. In a state where the specimen 102 is left at rest on the mounting unit 104, the emitting generator 101 emits an X-ray while being properly moved along the guide 102, thereby irradiating the specimen 120 with the X-ray from desired directions.

The detector 108 detects the radiation (X-ray in this case) emitted from the emitting generator 101 and passed through the specimen 120 mounted on the mounting unit 104 and through the mounting unit 104. The detector 108 detects, for example, both of the X ray passed through the specimen 120 and the X-ray passed through the space around the specimen 120.

A surface on the side of emitting generator 101, of the detector 108, that is, an X-ray detecting surface (detection surface) 108s has, for example, a rectangular outer shape and has an almost flat surface in which a number of sensors for detecting X rays are arranged two-dimensionally (for example, in a lattice shape). Therefore, radiation passed through the specimen 120 and the mounting unit 104 in the radiation emitted from the emitting generator 101 is detected by the detector 108, and a distribution of detection values of the radiation (in this case, a two-dimensional distribution having the lattice shape) is obtained.

The emitting generator 101, the guide 102, the mounting unit 104, and the detector 108 satisfy positional relations described below. Specifically, since the radiation range of the X ray emitted from the emitting generator 101 covers a wide range of the mounting unit 104, even when the emitting generator 101 moves to any of positions on the guide 102, the X ray emitted from any of the positions on the guide 102 is detected by the detector 108.

In FIG. 1, the guide 102 is formed almost in an arc shape, and the emitting generator 101 emits X ray toward the center point of the arc. The invention is not limited thereto. For example, the guide 102 may be extended almost linearly and the emitting generator 101 emits X ray in a direction almost perpendicular to the extending direction of the guide 102 even when the emitting generator 101 moves to any position on the guide 102. In any of the cases, radiation is sequentially emitted in a plurality of directions to a predetermined side (upper side in FIG. 1) of the specimen 120, and a distribution of detection values of the radiation (hereinafter, also called "radiation detection value distribution") is obtained.

On the other hand, the image capture control processing apparatus 200 has a configuration similar to that of a general personal computer and includes, mainly, a control unit 210, a display unit 220, an operating unit 230, and a storing unit 240.

The control unit 210 has a CPU 210a, a RAM 210b, and a ROM 210c, and controls the operations of the image capturing system 1 in a centralized manner. The control unit 210 realizes various functions and operations by reading a program PG stored in the storing unit 240 and executing the program PG.

The display unit 220 is constructed by, for example, a liquid crystal display and the like. Under control of the control unit 210, various images are visibly output. For example, a transmission image obtained by image capturing of the image capturing apparatus 100 or the like is visibly output.

More specifically, a planar image (plane image) and a stereoscopic image viewed from a specific direction are visibly output. Concretely, not only a plane image expressed by data of a transmission image (transmission image data) stored in the RAM 210b and the like but also a stereoscopic image expressed by stereoscopic image data generated by an image generating unit 216 (to be described later), other various image information, numerical information, and character information are displayed. Display of a stereoscopic image viewed from a specific direction as a two-dimensional image will be called "display of a stereoscopic image" hereinafter.

The operating unit 230 includes a keyboard and a mouse, accepts various inputs of the user, and transmits signals according to the inputs to the control unit 210.

The storing unit 240 includes a hard disk and the like, and stores, for example, the program PG for controlling various operations of the image capturing system 1, various data, and the like.

Functional Configuration in Control Unit

Figure 3:
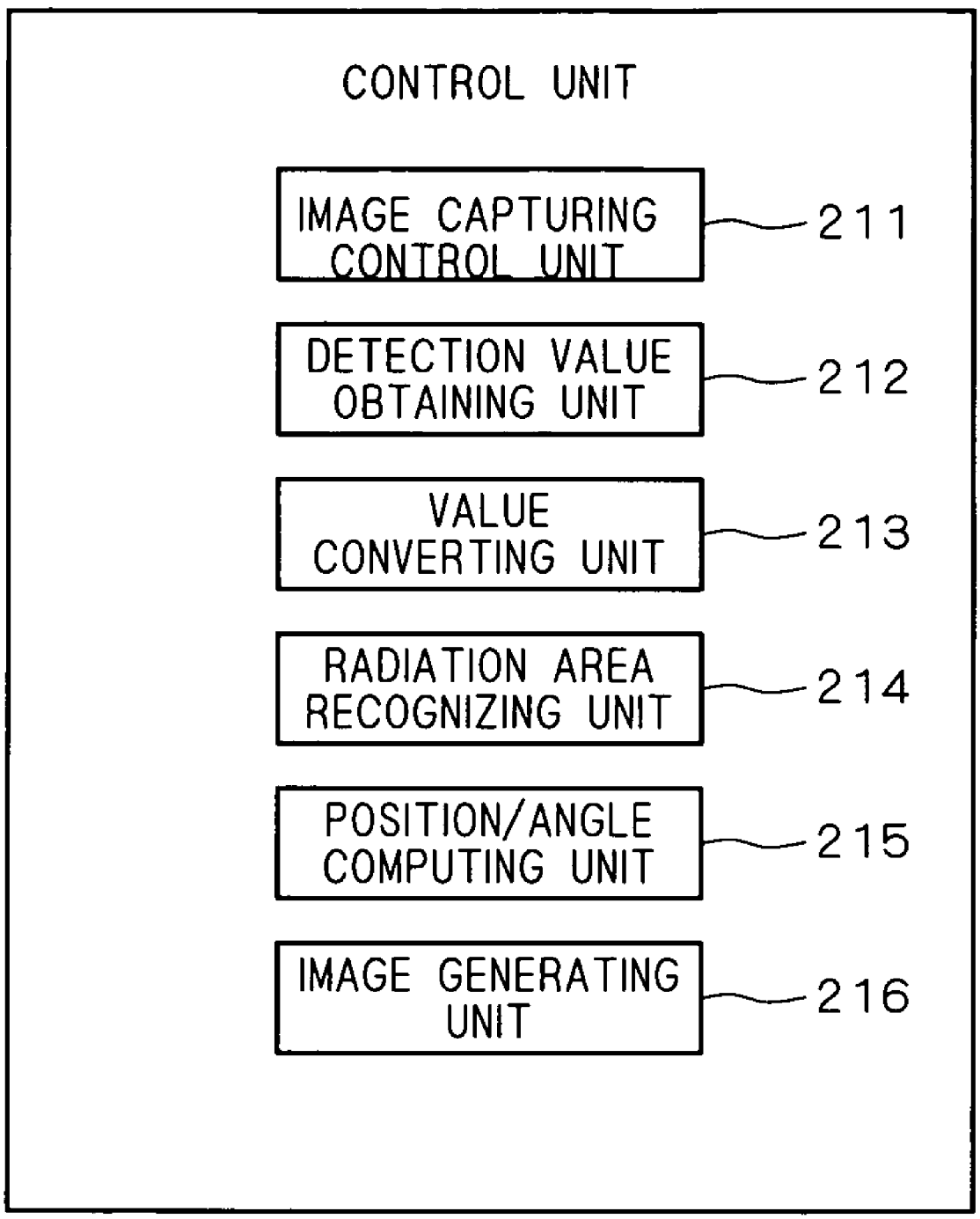
FIG. 3 is a diagram illustrating the functional configuration of a control unit in the first preferred embodiment.

FIG. 3 is a diagram illustrating the functional configuration realized when the program PG is executed by the control unit 210.

As shown in FIG. 3, the control unit 210 has, as functions, an image capturing control unit 211, a detection value obtaining unit 212, a value converting unit 213, a radiation area recognizing unit 214, a position/angle computing unit 215, and the image generating unit 216.

The image capturing control unit 211 controls operation of the image capturing apparatus 100. For example, the image capturing control unit 211 controls the position of the emitting generator 101 on the guide 102, thereby controlling the positional relation of the mounting unit 104, that is, the specimen 120 to the emitting generator 101 and the guide 102. By this, the spatial relation between the emitting generator 101 and the mounting unit 104 varies relatively. At this time, the distance between the emitting generator 101 and the detector 108 and the angle relation between the emitting generator 101 and the detector 108 are properly changed.

The "angle relation" includes the relation of the angle formed by the center line of radiation emitted from the emitting generator 101, that is, the radiation travel direction and the surface (detection surface) 108s in which a number of sensors are arranged in the detector 108.

The detection value obtaining unit 212 accepts and obtains a distribution of detection values of radiation detected by the detector 108. In the embodiment, a distribution of detection values detected by the sensors disposed two-dimensionally in the detection surface 108s, that is, a two-dimensional detection value distribution (two-dimensional distribution of the detection values) is obtained. The distribution of detection values obtained by the detection value obtaining unit 212 is temporarily stored in the RAM 210b or the storing unit 240.

The value converting unit 213 converts the distribution of the detection values obtained by the detection value obtaining unit 212 to a distribution of pixel values corresponding to a visible image (hereinafter, also called "pixel value distribution"), that is, image data. For example, a relatively large X-ray detection value is converted to a pixel value of low luminance (low tone), and a relatively small X-ray detection value is converted to a pixel value of high luminance (high tone). Image data (transmission image data, also called "transmission image") is a two-dimensional distribution of pixel values and temporarily stored in the RAM 210b or the storing unit 240.

By detecting radiation for a plurality of times by the detector 108 while changing the relative position and angle relations of the emitting generator 101 to the detector 108 by the image capturing control unit 211, a plurality of transmission images of the specimen 120 are obtained by the value converting unit 213.

The radiation area recognizing unit 214 recognizes the shape of an area irradiated with radiation (hereinafter also called "radiation area" or "radiation field") on the detection surface 108s from the emitting generator 101, concretely, the shape of the outer edges (hereinafter, also called "outer-edge shape") of the radiation area. A method of recognizing the outer-edge shape of the radiation area will be described later.

The position/angle computing unit 215 obtains the relative position relation and the relative angle relation between the emitting generator 101 and the detector 108 by computation on the basis of the outer-edge shape of the radiation area recognized by the radiation area recognizing unit 215 and the inner-edge shape of the diaphragm 101c. A method of computing the relative position relation and the relative angle relation will be described later.

The image generating unit 216 generates various images (for example, an image of a slice plane) by using the transmission images obtained by the value converting unit 213.

For example, when a distribution of a plurality of pixel values, that is, a plurality of transmission images are obtained while changing the position of the emitting generator 101 along the guide 102, the image generating unit 216 generates data of an image showing a slice plane (slice plane image) of the specimen 120 on the basis of the plurality of transmission images and the relative position relation and the relative angle relation of the emitting generator 101 to the detector 108 when the radiation of each of the transmission images is detected. The image generating unit 216 also generates data of a stereoscopic image of the specimen 120 having a three-dimensional structure on the basis of the data of the slice plane image.

Concretely, for example, the image generating unit 216 generates data of the slice plane image while temporarily storing the data of the transmission image into the RAM 210b in cooperation with the RAM 210b for temporarily storing data. Further, the image generating unit 216 generates data of the stereoscopic image while temporarily storing the data of the slice plane image into the RAM 210b. A method of generating the data of the slice plane image will be described later.

Method of Recognizing Outer-Edge Shape of Radiation Area

Figure 4:
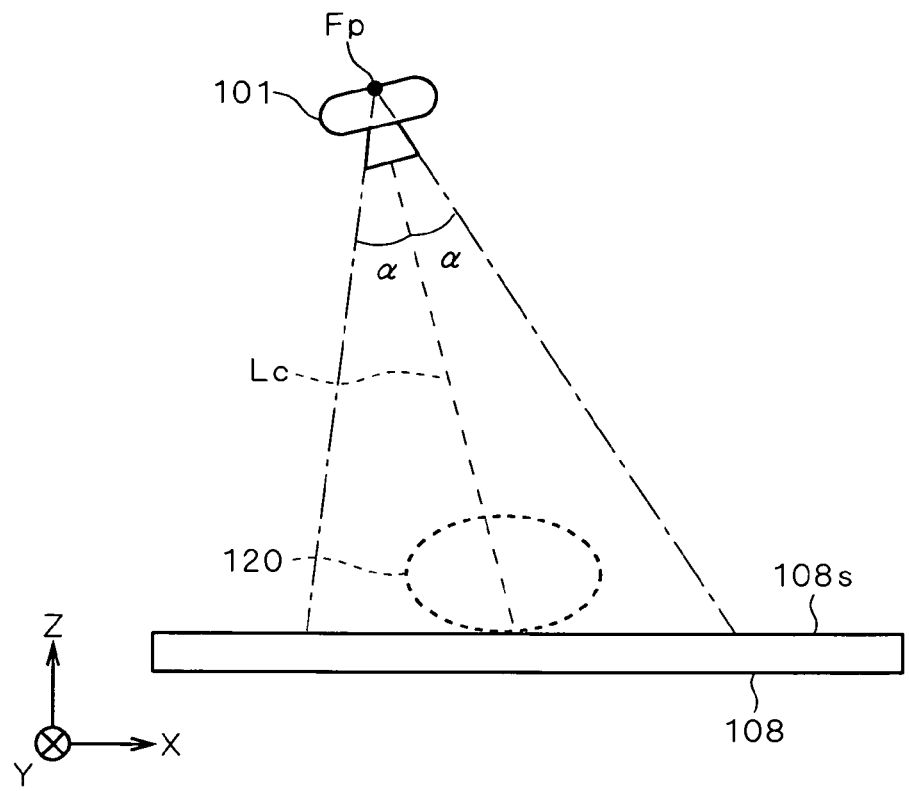
FIG. 4 is a diagram for explaining the principle of the method of recognizing an outer-edge shape of a radiation area.
Figure 5:
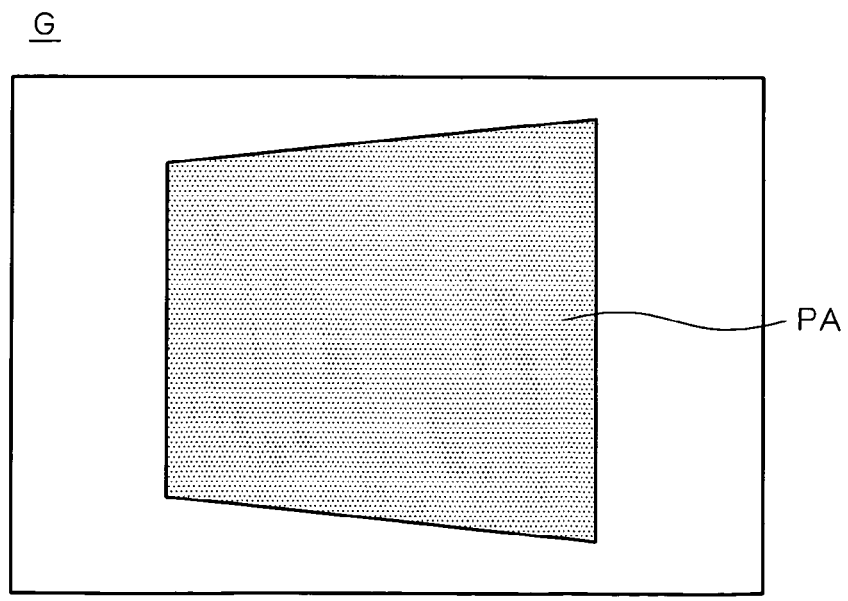
FIG. 5 is a diagram for explaining the principle of the method of recognizing the outer-edge shape of the radiation area.

FIGS. 4 and 5 are diagrams for explaining the principle of the method of recognizing the outer-edge shape of the radiation area in the radiation area recognizing unit 214.

FIG. 4 is a diagram paying attention to the emitting generator 101, the detector 108, and the specimen 120 at the time of imaging the specimen 120. In FIG. 4, the focal point Fp of the emitting generator 101 is shown by a filled circle, the outer edges of radiation emitted from the emitting generator 101 to the specimen 120 are shown by alternate long and short dash lines, and center line (center axis) Lc of the radiation emitted from the emitting generator 101 to the specimen 120 is shown by a broken line. It is assumed that each of the outer edges of the radiation emitted from the emitting generator 101 makes a predetermined angle α to the center axis Lc.

In FIG. 4, the direction of emitting radiation from the emitting generator 101 to the specimen 120, that is, the travel direction of radiation is inclined with respect to the normal line to the detection surface 108s. Image capturing performed by irradiating the detection surface 108s with radiation emitted obliquely will be also called "oblique image capturing".

FIG. 5 is a diagram illustrating a transmission image G obtained at the time of oblique image capturing as shown in FIG. 4. In the transmission image G, a pattern (trapezoidal image area which is shaded in the diagram) PA of the radiation emitted from the emitting generator 101 to the detection surface 108s appears. The pattern PA corresponds to the area irradiated with the radiation from the emitting generator 101 (radiation area) in the detection surface 108s.

In FIG. 5, the outer edges of the pattern PA form a trapezoidal shape. However, the invention is not limited thereto. For example, at the time of image capturing (facing-position image capturing) in which radiation is emitted from the emitting generator 101 in a state where the irradiation direction of the radiation from the emitting generator 101 toward the specimen 120 is almost perpendicular to the detection surface 108s and the detector 108 detects the radiation, thereby obtaining a distribution of detection values, the outer shape of the pattern PA is a square shape similar to the shape of the opening 101h.

For example, the radiation area recognizing unit 214 recognizes the pattern PA of the radiation from the transmission image G obtained by the value converter 213 and the outer-edge shape of the pattern PA, thereby recognizing the outer-edge shape of the radiation area of the radiation from the emitting generator 101 to the detection surface 108s. Concretely, the radiation area recognizing unit 214 recognizes the length of the upper base, the length of the lower base, and the height of the trapezoid as the outer-edge shape of the radiation area from the size of the detection surface 108s, the size of the projection image G, and the size of the pattern PA. That is, in the specification, the words "the outer-edge shape of the radiation area" are used for meaning including the size of the outer-edge shape, and the words "the inner-edge shape" are used for meaning including the size of the inner-edge shape.

Although the outer-edge shape of the radiation area is recognized from the transmission image G obtained by the value converting unit 213 in the embodiment, the invention is not limited thereto. For example, the outer-edge shape of the radiation area may be recognized from a distribution of detection values obtained by the detection value obtaining unit 212.

Principle of Deriving Position Relation and Angle Relation

FIGS. 6A and 6B to FIG. 9 are diagrams for explaining the principle of deriving the relative position relation and the relative angle relation between the emitting generator 101 and the detector 108 in the position/angle computing unit 215.

Figure 6A:
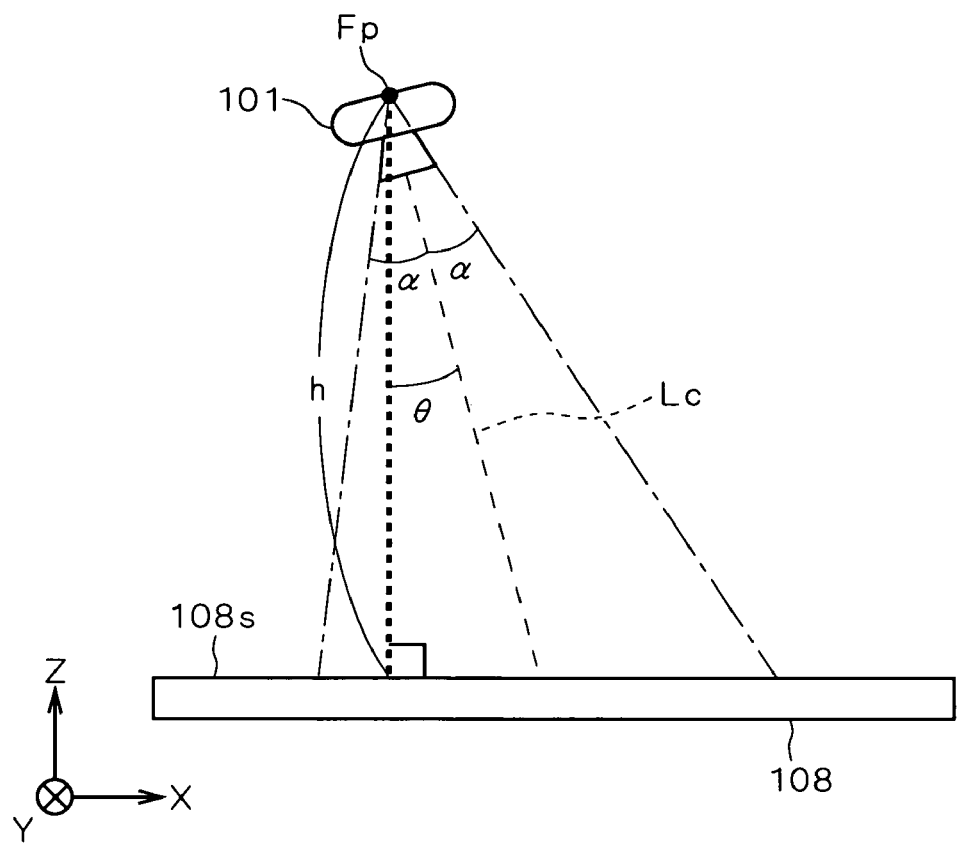
FIGS. 6A and 6B are diagrams for explaining the principle of deriving the position relation and the angle relation between the emitting generator and a detector.
Figure 6B:
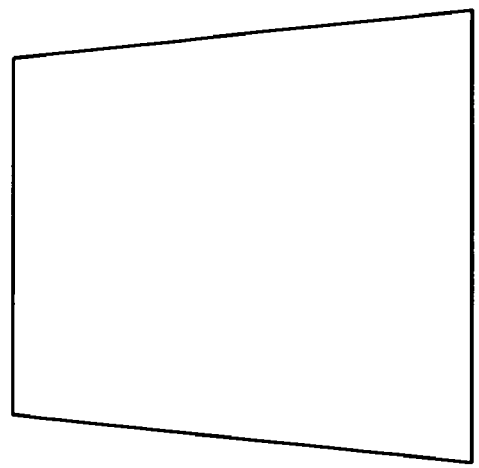

FIG. 6A is a sectional schematic view of the path of radiation seen from a side paying attention to the position relation between the emitting generator 101 and the detector 108. FIG. 6B is a diagram showing the outer-edge shape of the radiation area in the state of FIG. 6A.

The position/angle computing unit 215 computes the length of a perpendicular from the focal point Fp of the emitting generator 101 to the detection surface 108s, that is, distance "h" between the focal point Fp and the detection surface 108s, and angle θ formed by the center line Lc of the radiation emitted from the emitting generator 101 and a perpendicular from the focal point Fp to the detection surface 108s.

Figure 7A:
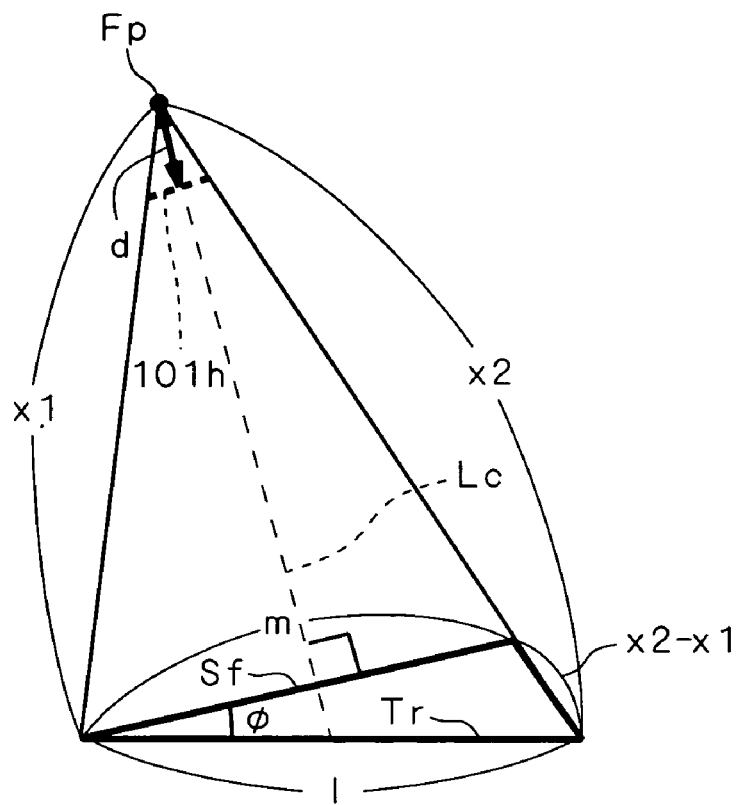
FIGS. 7A and 7B are diagrams for explaining the principle of deriving the position relation and the angle relation between the emitting generator and the detector.
Figure 7B:
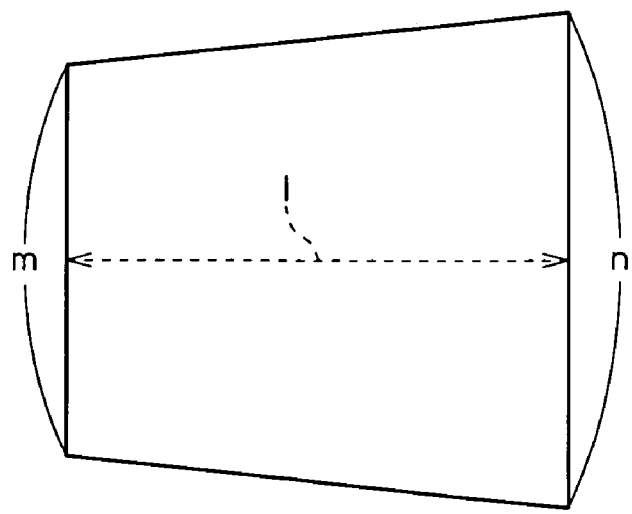

FIG. 7A is a diagram paying attention to the radiation path shown in FIG. 6A. FIG. 7B is a diagram paying attention to the outer-edge shape of the radiation area shown in FIG. 6B.

As shown in FIGS. 7A and 7B, the distance from the focal point Fp to the opening 101h is expressed as "d", the distance from the focal point Fp to the center point of the upper base of the trapezoid as the outer edges of the radiation area is expressed as x1, the distance from the focal point Fp to the center point of the lower base of the trapezoid as the outer edges of the radiation area is expressed as x2, the length of the upper base of the trapezoid as the outer edges of the radiation area is expressed as "m", the length of the lower base is expressed as "n", and the height is expressed as "l". The length of one side of the opening 101h is set as a predetermined value "a". Further, a square surface (virtual surface) Sf using the upper base of the trapezoid as the outer edges of the radiation area as one side and perpendicular to the center line Lc of the path of radiation is virtually set, and the angle formed between the detection surface 108s and the virtual surface Sf is expressed as φ.

Since the angle φ is the same as the angle θ, when the angle φ is obtained, the angle θ is obtained.

A method of calculating the angle φ (that is, the angle θ) and the distance "h" will be described concretely below.

The predetermined value "a" and the distance "d" are known in designing of the emitting generator 101. The length "m" of the upper base, the length "n" of the lower base, and the height "l" of the trapezoid as the outer-edge shape of the radiation area are recognized by the radiation area recognizing unit 214. The distance from the center point of one side on the lower base side of the trapezoid as the radiation area in the vertical surface Sf to the center point of the lower base of the trapezoid as the radiation area is calculated by "x2−x1".

Since the regular square pyramid using the focal point Fp as an apex and using the opening 101h as a bottom face and the regular square pyramid using the focal point Fp as an apex and using the virtual surface Sf as a bottom surface are similar figures, the distance x1 is obtained by the following equation (1).

$$x1 = \frac{m}{a}\sqrt{\left(\frac{a}{2}\right)^2 + d^2} = \frac{m}{a} \cdot L \quad \text{(Equation 1)}$$

$$\left(\text{wherein, } L = \sqrt{\left(\frac{a}{2}\right)^2 + d^2}\right)$$

Figure 8:
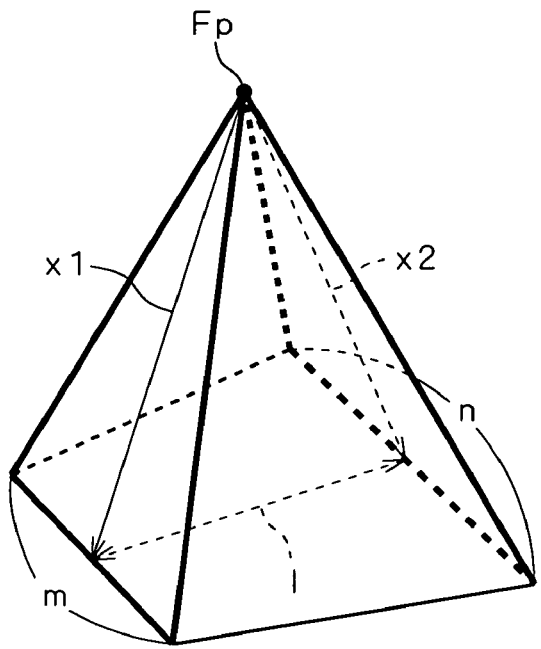
FIG. 8 is a diagram for explaining the principle of deriving the position relation and the angle relation between the emitting generator and the detector.

FIG. 8 is a perspective view of the path of radiation. As shown in FIG. 8, an isosceles triangle using the focal point Fp as an apex and the upper base of the trapezoid as the base, and an isosceles triangle using the focal point Fp as an apex and the lower base of the trapezoid as the base are similar figures, and the ratio of the sizes is m:n.

Since the relation of x1:x2=m:n is satisfied, the distance x2 is obtained by the following equation (2).

$$x2 = x1 \cdot \frac{n}{m} = \frac{n}{a} \cdot L \quad \text{(Equation 2)}$$

$$\left( \text{wherein, } L = \sqrt{\left(\frac{a}{2}\right)^2 + d^2} \right)$$

Therefore, the lengths (l, m, and x2−x1) of the three sides of a triangle Tr drawn by the thick lines in FIG. 7A are obtained. From the lengths of the three sides forming the triangle Tr, the three internal angles of the triangle Tr are unconditionally obtained. That is, the angle φ (that is, the angle θ) is obtained.

Figure 9:
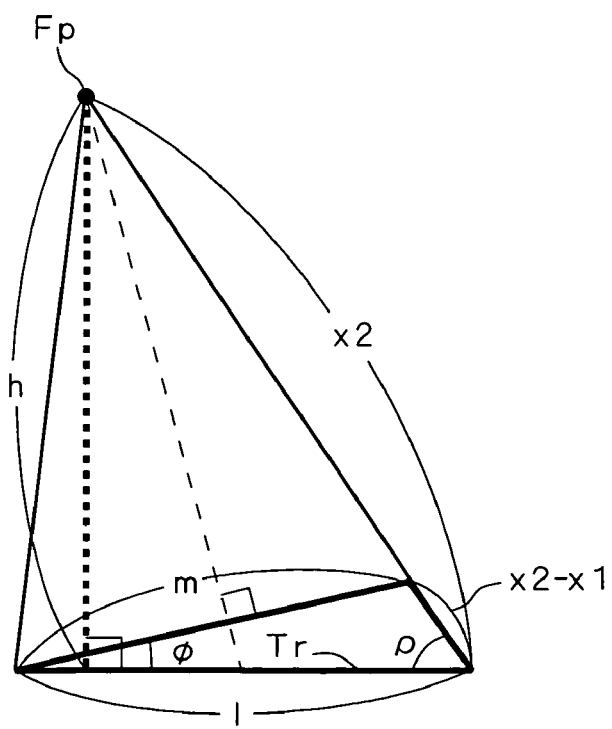
FIG. 9 is a diagram for explaining the principle of deriving the position relation and the angle relation between the emitting generator and the detector.

FIG. 9 is a diagram for explaining concrete calculation of the distance "h". In FIG. 9, a shape similar to that of FIG. 7A is drawn, and the triangle Tr drawn by the thick lines in FIG. 7A is similarly drawn by thick lines.

As described above, when the lengths (l, m, and x2−x1) of the three sides of the triangle Tr are obtained, the internal angle ρ of the upper base side of the trapezoid as the radiation area, as one of the internal angles of the triangle Tr, is also unconditionally obtained.

The distance "h" is obtained by the following equation (3).

$$h = x2 \cdot \sin \rho \quad \text{(Equation 3)}$$

When the distance "h" and the angle θ are obtained as described above, the relative position and angle relations between the emitting generator 101 and the detector 108 are obtained unconditionally. For example, the position (x, y, z) of the emitting generator 101 using a predetermined point (for example, center point) of the detection surface 108s as an original point is obtained.

Image Capturing Operation Flow

Figure 10:
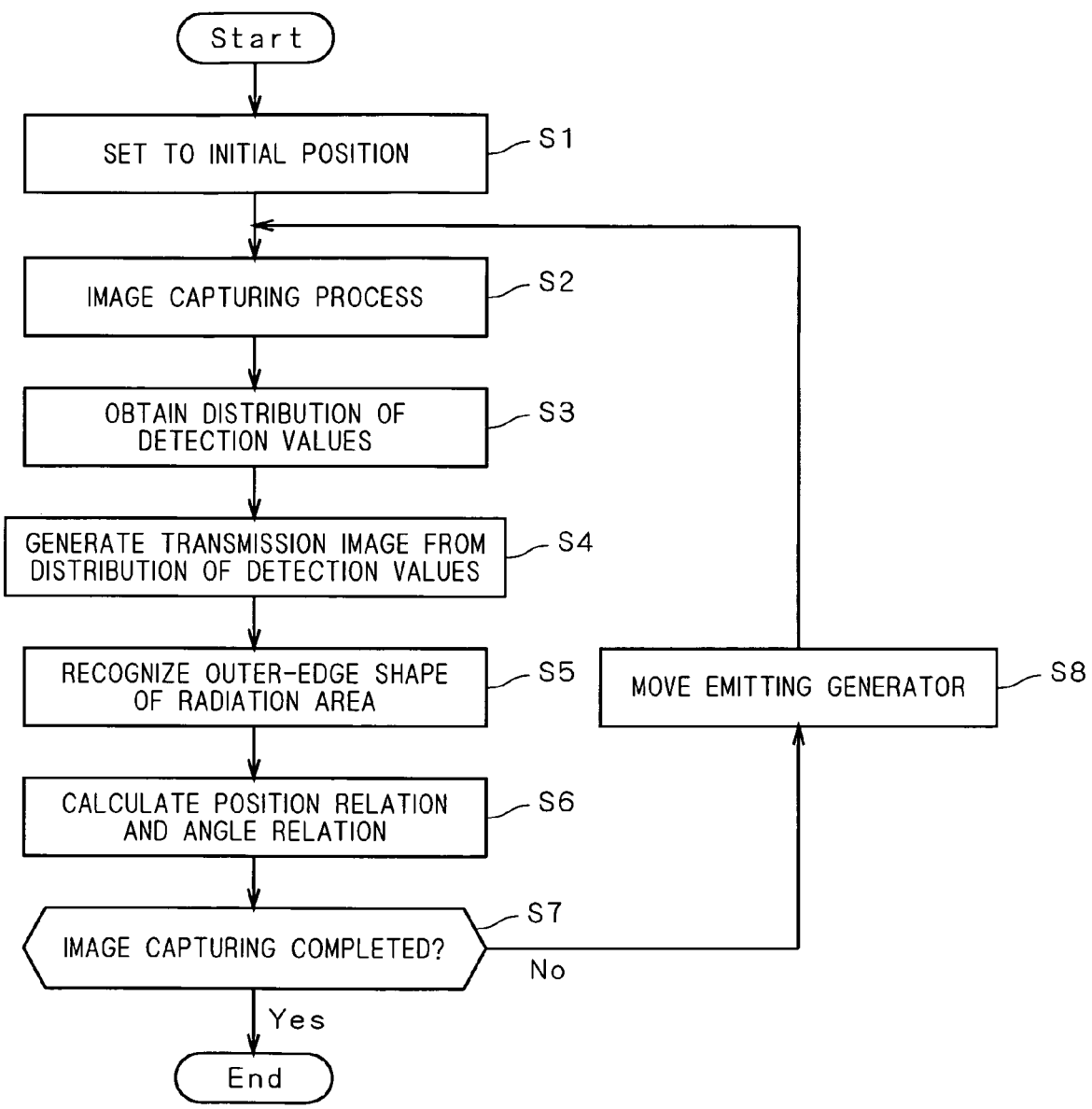
FIG. 10 is a flowchart showing an image capturing operation flow of the first preferred embodiment.

FIG. 10 is a flowchart showing an image capturing operation flow of continuously capturing transmission images of a plurality of frames while changing the radiation angle of X ray from the emitting generator 101 to the specimen 120 in multiple stages in the image capturing system 1. The operation flow is realized under control of, mainly, the image capturing control unit 211 when the control unit 210 executes the program PG. The operation flow starts when the specimen 120 is mounted on the mounting unit 104 and a predetermined input is entered from the operating unit 230.

First, in step S1, by the control of the image capturing control unit 211, the emitting generator 101 is set in an initial position.

The initial position of the emitting generator 101 on the guide 102 is preset. It is assumed here that the initial position is set so that the irradiation angle of X ray from the emitting generator 101 to the specimen 120 is the smallest. Concretely, the emitting generator 101 is disposed, for example, at one end in the extending direction of the guide 102 (the right end in FIG. 1).

In step S2, by the control of the image capturing control unit 211, image capturing process is performed. The image capturing process is performed here by emitting radiation from the emitting generator 101 to the specimen 120 and detecting the radiation by the detector 108.

In step S3, on the basis of detection values of the radiation obtained by the sensors in the detector 108 in step S2, the detection value obtaining unit 212 obtains a two-dimensional distribution of the detection values.

In step S4, the value converting unit 213 converts the two-dimensional distribution of the detection values obtained in step S3 to a two-dimensional distribution of pixel values, thereby generating a transmission image.

In step S5, from the transmission image obtained in step S4, the radiation area recognizing unit 214 recognizes the outer-edge shape (concretely, the size) of the radiation area irradiated with the radiation in the detection surface 108s. For example, the pattern PA corresponding to the radiation area is recognized from the transmission image G as shown in FIG. 5, and the shape and size of the outer edges are recognized.

In step S6, on the basis of the outer-edge shape of the radiation area recognized in step S5 and the inner-edge shape of the diaphragm 101c, the position/angle computing unit 215 calculates the relative position relation and the relative angle relation between the emitting generator 101 and the detector 108. For example, by a method as described with reference to FIGS. 6A to 9, the distance "h" and the angle θ are calculated, and the relative position and angle relations between the emitting generator 101 and the detector 108 are unconditionally calculated from the distance "h" and the angle θ.

In step S7, whether the image capturing is finished or not is determined. For example, when a predetermined parameter reaches a predetermined value, it is determined to finish the image capturing.

Concretely, until the predetermined parameter reaches the predetermined value, the emitting generator 101 is moved along the guide 102 in step S8, and the program returns to step S2. On the other hand, when the predetermined parameter reaches the predetermined value, the operation flow is finished.

At this time, a predetermined number of transmission images are sequentially obtained, and the relative position relation and the relative angle relation between the emitting generator 101 and the detector 108 in each of image capturing processes corresponding to the transmission images are calculated. Information indicative of the relative position relation and the relative angle relation between the emitting generator 101 and the detector 108 is associated with the transmission image data and stored in the RAM 210b or the storing unit 240.

The predetermined parameters are the number of image capturing times, the travel distance of the emitting generator 101, the travel angle of the emitting generator 101, and the like. For example, until the number of image capturing times reaches a predetermined number (for example, 19), the processes in steps S2 to S8 are repeated. After the number of image capturing times reaches the predetermined number (for example, 19), the operation flow is finished.

In step S8, by the control of the image capturing control unit 211, the emitting generator 101 is moved along the guide 102. The position of the emitting generator 101 on the guide 102 is changed from the position in the image capturing process of last time to the next position. For example, in the case where the travel range along the extending direction of the guide 102 is divided in 18 parts and the emitting generator 101 moves in multiple stages, in step S8, the emitting generator 101 travels in the distance of 1/18 of the travel range.

Principle of Generation of Slice Plane Image Data

As described above, in the case where the position of the emitting generator 101 is varied along the guide 102 and a plurality of transmission images are obtained sequentially, for example, by the image generating unit 216, data of slice plane images (slice plane image data) of the specimen 120 is properly generated.

The principle of generating the slice plane image data, that is, the principle of tomosynthesis in the image generating unit 216 will be described.

FIGS. 11 and 12 are schematic diagrams showing the principle of tomosynthesis.

In the tomosynthesis, radiation, concretely, X ray passing through the specimen 120 is emitted at different angles on the side of one direction of the specimen 120 to the specimen 120 and data of a plurality of transmission images is obtained and synthesized, thereby obtaining an image of a slice plane. The case where a star-shaped element 121 and a round-shaped element 122 schematically showing internal structures (concretely, a human organ, a lesioned part, and the like) of the specimen 120 are arranged in the direction perpendicular to the detection surface 108s as shown in FIG. 11 will be described as an example.

As shown in FIG. 11, by emitting radiation to the specimen 120 at different angles, data of a plurality of transmission images is obtained. In transmission images 41, 42, and 43 expressed by the data of the plurality of transmission images obtained in such a manner, the positions of images of the elements vary according to the distance (height) from the detection surface 108s. While utilizing the phenomenon, arbitrary slice plane image data is generated by using a known method of synthesizing a plurality of images. One of the known methods of synthesizing a plurality of images in tomosynthesis is shift-and-add algorithm.

In shift-and-add algorithm, on the basis of the plurality of transmission images 41 to 43 and the positions (x, y, z) and angles of the emitting generator 101 on detection of radiations corresponding to the transmission images 41 to 43 (that is, in the image capturing process), a process of sequentially adding the transmission images while shifting the relative positions of the transmission images 41 to 43 is performed.

For example, as shown in FIG. 12A, an image 51 in which the star-shaped element 121 which is vague in the transmission images 41 to 43 is emphasized is obtained. As shown in FIG. 12B, an image 52 in which the round-shaped element 122 which is vague in the transmission images 41 to 43 is emphasized is obtained. The image 51 is a slice plane image obtained by emphasizing a cross section at height where the star-shaped element 121 exists in the internal structure of the specimen 120. The image 52 is a slice plane image obtained by emphasizing a cross section at height where the round-shaped element 122 exists in the internal structure of the specimen 120.

The example of generating the images 51 and 52 by synthesizing the three transmission images 41 to 43 by addition has been described to simplify the explanation. In practice, a number of transmission images are obtained and synthesized.

As described above, in the image capturing system 1 of the first preferred embodiment of the invention, on the basis of the outer-edge shape of the radiation area irradiated with radiation on the detection surface 108s and the inner-edge shape of a predetermined member (for example, the diaphragm 101c) specifying the path of radiation, the relative position relation and the relative angle relation of the emitting generator 101 to the detector 108 are obtained. That is, at the time of actual image capturing, the relative position and angle relations of the emitting generator 101 with respect to the detector 108 are obtained. Consequently, the position and angle of the emitting generator 101 at the time of image capturing can be grasped accurately.

On the basis of the outer-edge shape of the radiation area irradiated with ration on the detection surface 108s and the inner-edge shape of the diaphragm 101c generally used, the relative position and angle relations of the emitting generator 101 with respect to the detector 108 are obtained. Consequently, without adding a special configuration that specifies the path of radiation, the position and angle of the emitting generator 101 at the time of image capturing can be grasped accurately.

The outer-edge shape of the radiation area irradiated with radiation on the detection surface 108s is recognized from the transmission images. Therefore, without adding a special configuration, the outer-edge shape of the radiation area is recognized.

Using the information indicative of the accurately grasped position and angle of the emitting generator 101 in the image capturing, a slice plane image is generated on the basis of a plurality of transmission images. Consequently, a high-quality slice plane image in which occurrence of so-called artifact is suppressed is obtained.

Second Preferred Embodiment

In the image capturing system 1 of the first preferred embodiment, the outer-edge shape of the radiation area is recognized from the transmission images. On the other hand, in an image capturing system 1A of a second preferred embodiment, an irradiation area on the detection surface 108s is illuminated by lighting and is photographed by a camera. The outer-edge shape of the radiation area is recognized from obtained photographed images.

The image capturing system 1A of the second preferred embodiment will be described below. The image capturing system 1A of the second preferred embodiment has a configuration similar to that of the image capturing system 1 of the first preferred embodiment except for the configuration of recognizing the outer-edge shape of the radiation area. Consequently, the same reference numerals are designated to the similar components and their description will not be repeated. Mainly, the different configuration will be described.

FIG. 13 is a diagram showing a schematic configuration of the image capturing system 1A according to the second preferred embodiment of the present invention.

The image capturing system 1A includes: an image capturing apparatus 100A which has a emitting generator 101A to which an illuminating mechanism 101p (FIG. 14) is added in place of the emitting generator 101 of the first preferred embodiment and a camera unit 106; and an image capture control processing apparatus 200A including a control unit 210A having a functional configuration of recognizing the outer-edge shape of the radiation area different from that of the control unit 210 of the first preferred embodiment. A program PGA is stored in place of the program PG in the storing unit 240.

Figure 14:
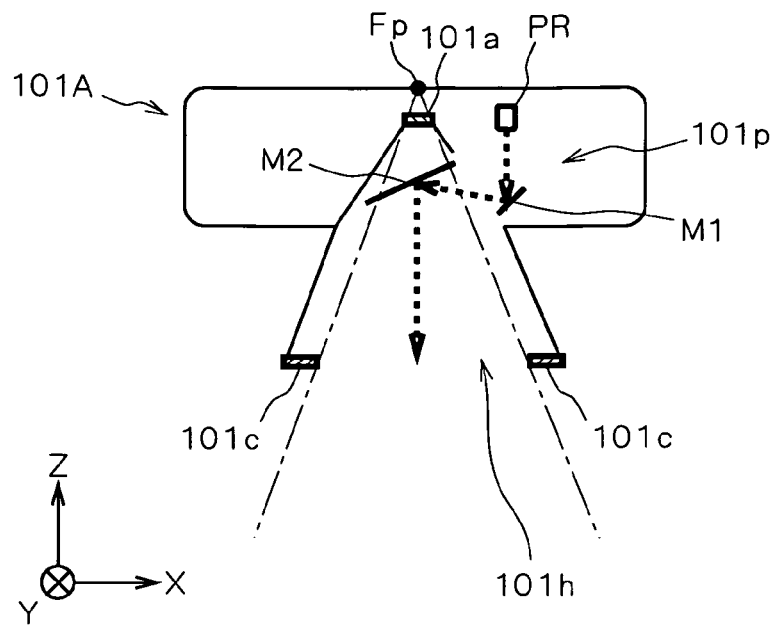
FIG. 14 is a diagram for explaining the configuration of a emitting generator in the second preferred embodiment.

FIG. 14 is a cross section diagram schematically showing the configuration of the emitting generator 101A. The emitting generator 101A is constructed by, for example, an X-ray tube and has the generating unit 101a, the diaphragm 101c, and the illuminating mechanism 101p. That is, the emitting generator 101A is obtained by adding the illuminating mechanism 101p to the emitting generator 101 of the first preferred embodiment.

The illuminating mechanism 101p is provided near the generating unit 101a and has a light source PR, a first reflection mirror M1, and a second reflection mirror M2.

The light source PR has an apparatus for generating a visible light ray and generates, for example, a laser beam of a predetermined color. The first reflection mirror M1 reflects the light from the light source PR toward the second reflection mirror M2. The second reflection mirror M2 reflects the light from the first reflection mirror M1, and light is emitted from the opening 101h in the diaphragm 101c to the detection surface 108s. In FIG. 14, the path of light from the light source PR is shown by a thick broken-line arrow.

The path (optical path) of light generated by the light source PR and emitted via the diaphragm 101c (concretely, the opening 101h) is set almost the same as the path (radiation path) of radiation emitted from the generator 101a via the diaphragm 101c (concretely, the opening 101h). That is, the illuminating mechanism 101p is constructed so that light generated from the light source PR is applied to the detection surface 108s via the optical path which is almost the same as the radiation path via the diaphragm 101c.

In the second preferred embodiment, the mounting unit 104 is made of a material which transmits a visible light ray such as transparent glass so that the light is not blocked by the mounting unit 104. Further, since the second reflection mirror M2 is disposed on a path of radiation extending from the generating unit 101a to the diaphragm 101c (concretely, the opening 101h), it is made of a material which easily transmits radiation.

The camera unit 106 is a sensor constructed by, for example, a digital camera including an image capturing device such as a CCD, and is mounted just above the mounting unit 104. Concretely, the optical axis of a taking lens of the camera unit 106 is almost orthogonal to the detection surface 108s and passes almost the center of the detection surface 108s. That is, the camera unit 106 is mounted so as to face the detection surface 108s.

More specifically, as shown in FIG. 13, the camera unit 106 is disposed, for example, in a position around the center in the extending direction of the guide 102 (for example, in FIG. 13, near the emitting generator 101A drawn by the solid line) so as not to disturb the travel of the emitting generator 101A, the path of radiation emitted from the emitting generator 101A, and the optical path of light emitted from the illuminating mechanism 101p.

The detection surface 108s illuminated with the light from the illuminating mechanism 101p is photographed from just above by the camera unit 106 in the image capturing process using radiation, thereby obtaining an image. The image is transmitted to the control unit 210A.

Figure 15:
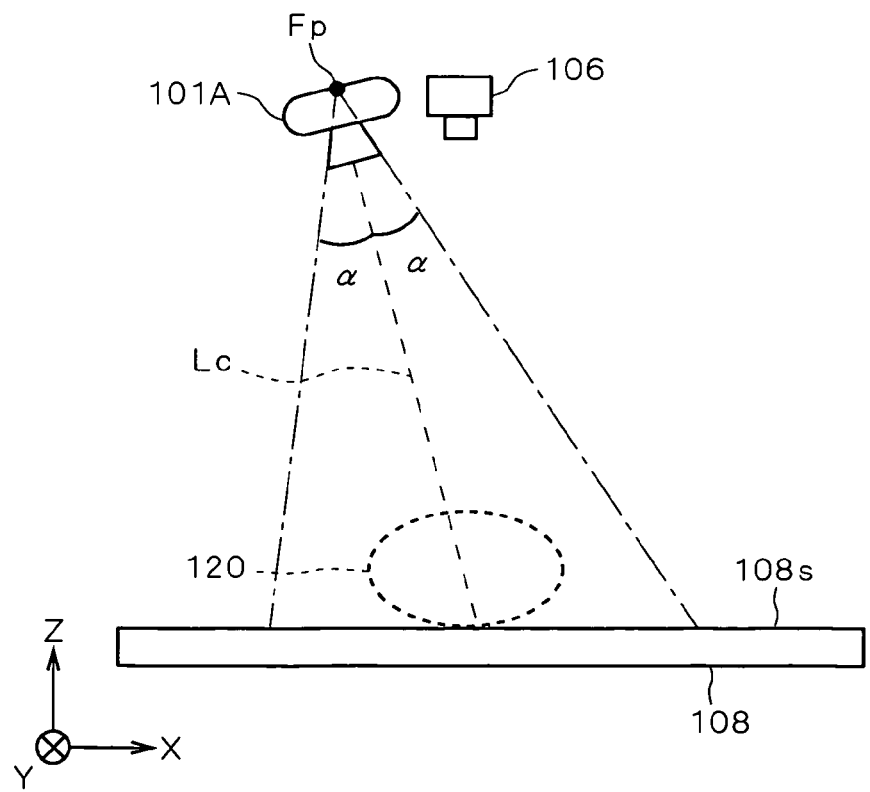
FIG. 15 is a diagram for explaining the principle of a method of recognizing the outer-edge shape of the radiation area.

FIG. 15 is a diagram paying attention to the emitting generator 101A, the detector 108, the specimen 120, and the camera unit 106 at the time of imaging the specimen 120. As shown in FIG. 15, the position and the image capturing direction of the camera unit 106 are fixed. The camera unit 106 photographs the detection surface 108s from a predetermined position irrespective of the position of the emitting generator 101A on the guide 102.

The image obtained by the camera unit 106 has a pattern similar to that of the transmission image G shown in FIG. 5 at the time of, for example, oblique imaging capturing as shown in FIG. 15. Specifically, the outer edges of the detection surface 108s corresponding to the outer edges of the transmission image G and the area (illuminated area) illuminated by light from the illuminating mechanism 101p corresponding to the pattern PA are captured.

The functional configuration of the control unit 210A will now be described.

Figure 16:
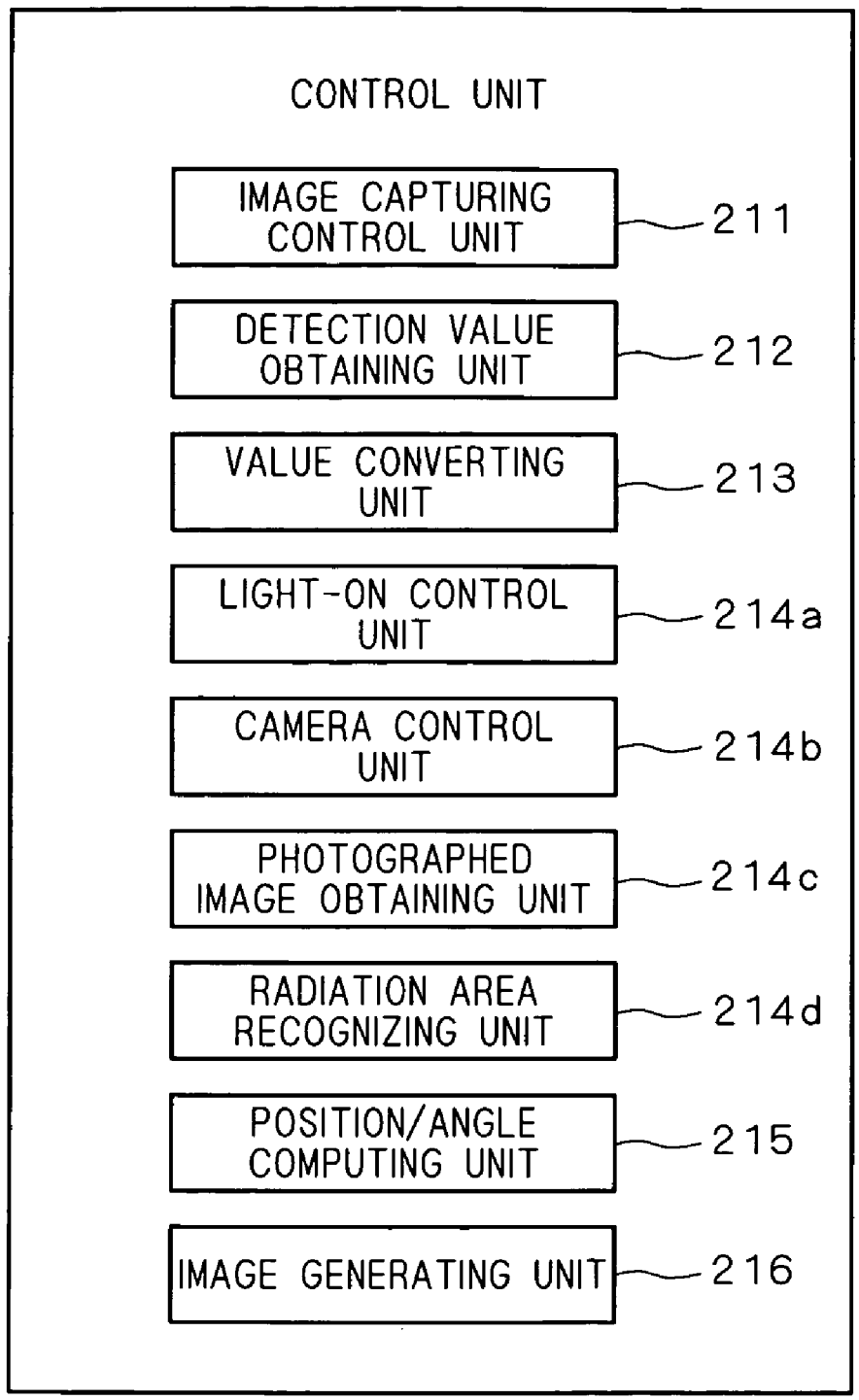
FIG. 16 is a diagram illustrating the functional configuration of a control unit in the second preferred embodiment.

FIG. 16 is a diagram illustrating the functional configuration realized when the program PGA is executed by the control unit 210A.

As shown in FIG. 16, the control unit 210A has, as functions, the image capturing control unit 211, the detection value obtaining unit 212, the value converting unit 213, a light-on control unit 214a, a camera control unit 214b, a photographed-image obtaining unit 214c, a radiation area recognizing unit 214d, the position/angle computing unit 215, and the image generating unit 216.

The image capturing control unit 211, the detection value obtaining unit 212, the value converting unit 213, the position/angle computing unit 215, and the image generating unit 216 are similar to those of the first preferred embodiment.

The light-on control unit 214a controls light-on of the illuminating mechanism 101p, that is, emission of light from the light source PR.

The camera control unit 214b controls the operation of the camera unit 106. For example, light from the illuminating mechanism 101p is emitted to the radiation area by the light-on control unit 214a in accordance with image capturing using radiation and the area is photographed by the camera unit 106 to obtain a photographed image.

The photographed-image obtaining unit 214c receives the photographed image obtained by the camera unit 106. In the photographed-image obtaining unit 214c, a necessary image process may be performed.

The radiation area recognizing unit 214d recognizes the outer-edge shape of the radiation area irradiated with radiation on the detection surface 108s emitted from the emitting generator 101A in a manner similar to the radiation area recognizing unit 214 of the first preferred embodiment except for a recognizing method.

The radiation area recognizing unit 214d recognizes the outer-edge shape of the radiation area in the photographed image obtained by the photographed-image obtaining unit 214c.

Specifically, the radiation area recognizing unit 214d recognizes an area irradiated with light in the detection surface 108s by detecting, for example, a predetermined color or a high-illuminance part in the photographed image obtained by the photographed-image obtaining unit 214c. The radiation area recognizing unit 214d also recognizes the outer edges of the detection surface 108s by, for example, edge detection. From the size of the detection surface 108s and the size of the area irradiated with light, the length of the upper base, the length of the lower base, and the height of the trapezoid as the outer-edge shape of the radiation area are recognized.

In the position/angle computing unit 215 and the image generating unit 216, processes similar to those of the first preferred embodiment are performed by using the recognition results of the radiation area recognizing unit 214d.

Figure 17:
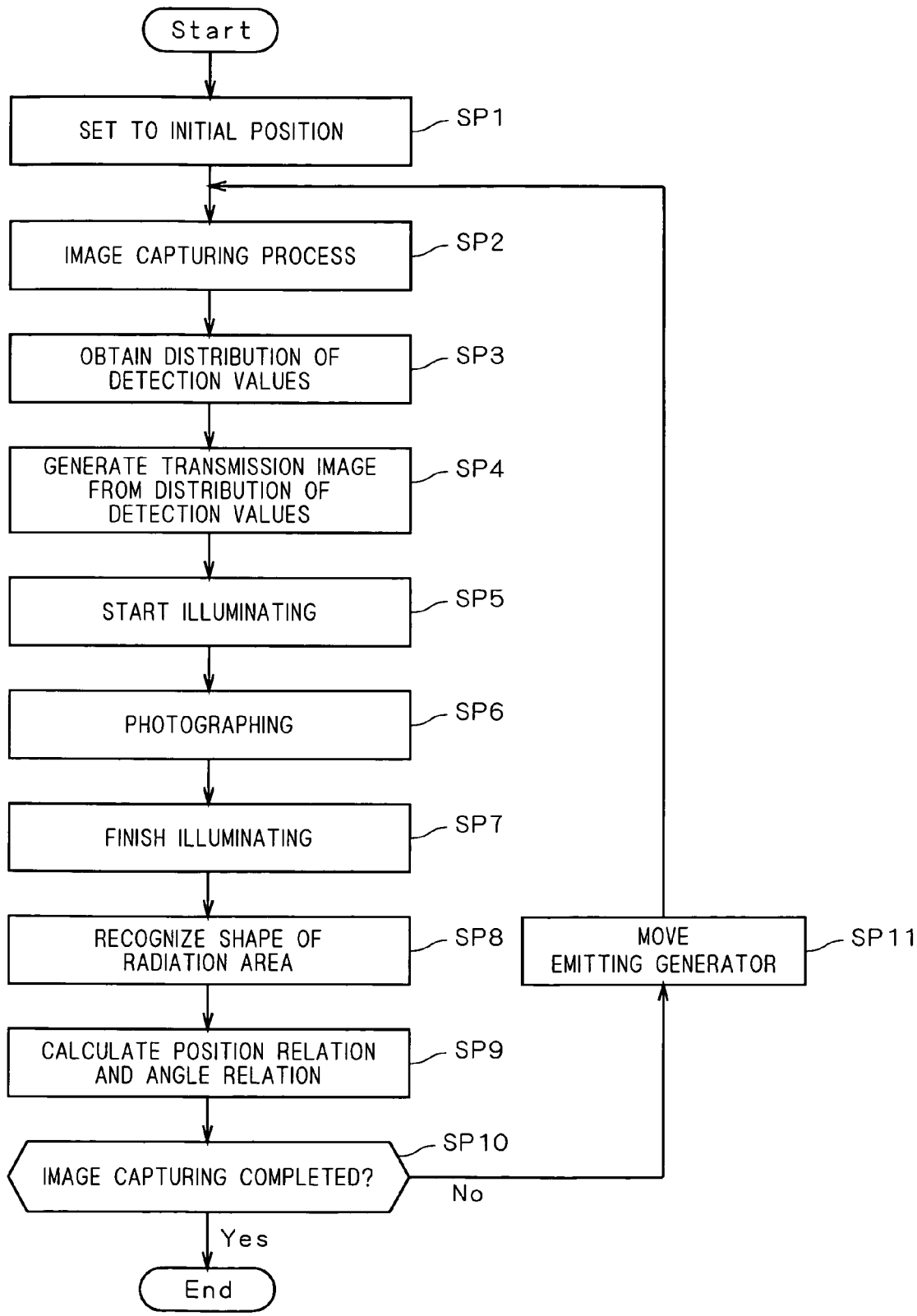
FIG. 17 is a flowchart showing an image capturing operation flow in the second preferred embodiment.

FIG. 17 is a flowchart showing an image capturing operation flow of continuously capturing transmission images of a plurality of frames while changing the radiation angle of X ray from the emitting generator 101A to the specimen 120 in multiple stages in the image capturing system 1A. The operation flow is realized under control of, mainly, the image capturing control unit 211 when the control unit 210A executes the program PGA. The operation flow starts when the specimen 120 is mounted on the mounting unit 104 and a predetermined input is entered from the operating unit 230.

In steps SP1 to SP4, processes similar to those in steps S1 to S4 in FIG. 10 are performed.

In step SP5, under control of the light-on control unit 214a, irradiation (illuminating) of the detection surface 108s with light by the illuminating mechanism 101p starts.

In step SP6, under control of the camera control unit 214b, photographing by the camera unit 106 is performed. A photographed image of the detection surface 108s irradiated with light is obtained by the photographed-image obtaining unit 214c.

In step SP7, under control of the light-on control unit 214a, the irradiation (illuminating) of the detection surface 108s with light by the illuminating mechanism 101p is finished.

In step SP8, the radiation area recognizing unit 214d recognizes the outer-edge shape (concretely, the size) of the radiation area irradiated with radiation in the detection surface 108s from the photographed image obtained in step SP6.

In steps SP9 to SP11, processes similar to those of steps S6 to S8 in FIG. 10 are performed.

As described above, in the image capturing system 1A of the second preferred embodiment of the invention, in a manner similar to the image capturing system 1 of the first preferred embodiment, the relative position relation and the relative angle relation of the emitting generator 101A with respect to the detector 108 are obtained on the basis of the outer-edge shape of the radiation area irradiated with radiation on the detection surface 108s and the inner-edge shape of the predetermined member (for example, the diaphragm 101c) that specifies the path of radiation. Consequently, the position and angle of the emitting generator 101A at the time of image capturing can be grasped accurately.

MODIFICATIONS

Although the embodiments of the present invention have been described above, the invention is not limited to the above description.

For example, in the foregoing embodiment, a slice plane image is generated by using the shift-and-add algorism. The invention is not limited thereto. For example, while changing the radiation angle of X ray from the emitting generator 101 to the specimen 120 in multiple stages, a plurality of transmission images obtained are regarded as a part of transmission images obtained by the CT (Computed Tomography) image capturing technique. A slice plane image may be generated by using a known filtered back projection method (FBPM) or the like as the technique of CT.

Although the inner-edge shape of a predetermined member (for example, the diaphragm 101c) is a square and the outer-edge shape of the radiation area is a trapezoid or square in the foregoing embodiments, the invention is not limited thereto. When each of the inner-edge shape of the predetermined member (for example, the diaphragm 101c) and the outer-edge shape of the radiation area is a shape having four or more vertexes such as a rectangular or trapezoid, the distance "h" and the angle θ can be obtained by a computing method similar to that of the embodiment.

Although the distance "d" from the focal point Fp to the opening 101h is determined in designing in the foregoing embodiments, the invention is not limited to the method. For example, when the distance "h" at the angle θ=0 is known, the distance "d" may be unconditionally calculated from the size of the radiation area (for example, square) at that time and the size of the inner-edge shape of the diaphragm 101c.

In the second preferred embodiment, the detection surface 108s is irradiated with visible light from the illuminating mechanism 101p and photographed by the camera unit 106, thereby obtaining a photographed image. The invention however is not limited to the embodiment. It is also possible to irradiate the detection surface 108s with other light such as infrared light and obtain a photographed image by using an infrared camera or the like. To reduce an error in calculation in the distance "h" an the angle θ, preferably, the linearity of light is high to some extent. For example, infrared light or light having a wavelength shorter than that of the infrared light is desirable.

While the invention has been shown and described in detail, the foregoing description is in all aspects illustrative and not restrictive. It is therefore understood that numerous modifications and variations can be devised without departing from the scope of the invention.

What is claimed is:

1. A transmission image capturing system comprising:
   a generator for generating radiation;
   a predetermined member for specifying a radiation path of said radiation by its inner-edge shape;
   a detector for detecting radiation emitted from said generator and passing through a specimen via said predetermined member;
   an obtaining unit for obtaining a plurality of transmission images of said specimen by detecting the radiation for a plurality of times by said detector while changing a relative position relation and a relative angle relation of said generator to said detector; and
   a computing unit configured to obtain said relative position and angle relations on the basis of an outer-edge shape of a radiation area which is irradiated with the radiation emitted from said generator to a detection surface of said detector and the inner-edge shape of said predetermined member.

2. The transmission image capturing system according to claim 1, wherein said predetermined member includes a diaphragm provided for said generator.

3. The transmission image capturing system according to claim 1, wherein each of the outer-edge shape of said radiation area and the inner-edge shape of said predetermined member has four or more vertexes.

4. The transmission image capturing system according to claim 1, wherein the inner-edge shape of said predetermined member includes a rectangular shape, and the outer-edge shape of said radiation area includes a trapezoid.

5. The transmission image capturing system according to claim 1, further comprising a recognizing unit for recognizing the outer-edge shape of each of said radiation areas from said transmission images.

6. The transmission image capturing system according to claim 1, comprising:
   a light beam irradiating unit for irradiating said detection surface with a light beam generated from a light source provided near said generator via said predetermined member along an optical path which is almost the same as said radiation path;
   an image capturing unit for obtaining a photographed image by photographing said detection surface irradiated with said light beam; and
   a recognizing unit for recognizing an outer-edge shape of said radiation area from said photographed image.

7. The transmission image capturing system according to claim 1, further comprising a generator for generating a slice plane image of said specimen on the basis of said plurality of transmission images by using said relative position and angle relations obtained by said computing unit and corresponding to said transmission images.

8. A transmission image capturing method of obtaining a plurality of transmission images by detecting radiation emitted from a generator and passing through a specimen via a predetermined member for a plurality of times by a detector while changing a relative position relation and a relative angle relation of said generator to said detector, comprising the steps of:
   (a) recognizing an outer-edge shape of a radiation area irradiated with radiation on a detection surface of said detector from said generator; and
   (b) obtaining said relative position and angle relations on the basis of the outer-edge shape of said radiation area and the inner-edge shape of said predetermined member.

* * * * *